(12) United States Patent
Alleyne

(10) Patent No.: US 6,718,044 B1
(45) Date of Patent: Apr. 6, 2004

(54) FETAL COMMUNICATION APPARATUS

(76) Inventor: Neville Alleyne, 9687 Claiborne Square, La Jolla, CA (US) 92037

( * ) Notice: Subject to any disclaimer, the term of this patent is extended or adjusted under 35 U.S.C. 154(b) by 0 days.

(21) Appl. No.: 09/089,247

(22) Filed: Jun. 2, 1998

(51) Int. Cl.[7] .............................. H04R 1/02; H04R 9/06; A61M 21/00
(52) U.S. Cl. ........................ 381/336; 333/388; 600/28
(58) Field of Search .............................. 381/56, 57, 58, 381/59, 301, 74, 332, 333, 92, 104, 107, 109, 111, 122, 355, 334, 151, 150, 385, 328, FOR 125, 165; 600/587, 591, 27, 28; 224/910, 930; 434/309

(56) References Cited

U.S. PATENT DOCUMENTS

| | | | |
|---|---|---|---|
| 3,934,085 A | * | 1/1976 | Munson et al. ............... 381/57 |
| 4,319,081 A | * | 3/1982 | Martin et al. ................. 381/56 |
| 4,382,793 A | | 5/1983 | Anderson |
| 4,798,539 A | * | 1/1989 | Henry et al. ................. 434/319 |
| 4,815,143 A | * | 3/1989 | Derhaag et al. ............. 381/361 |
| 4,827,458 A | * | 5/1989 | D'Alayer De Costemore D'Arc .......................... 381/57 |
| 4,830,007 A | | 5/1989 | Stein |
| 4,934,998 A | | 6/1990 | Thomas, Jr. |
| 5,063,912 A | * | 11/1991 | Hughes ....................... 128/33 |
| 5,109,421 A | | 4/1992 | Fox |
| 5,303,371 A | * | 4/1994 | Nakajima .................... 381/109 |
| 5,420,581 A | * | 5/1995 | Peter et al. .................. 340/573 |
| 5,450,494 A | * | 9/1995 | Okubo et al. ................ 381/57 |
| 5,491,756 A | | 2/1996 | Francais |
| 5,495,357 A | * | 2/1996 | Osterhout ................... 381/172 |
| 5,532,681 A | * | 7/1996 | Peters et al. ................ 340/573 |
| 5,699,558 A | * | 12/1997 | Min .............................. 381/332 |
| 5,764,776 A | * | 6/1998 | Francais ..................... 381/332 |
| 5,827,173 A | * | 10/1998 | Lindsay ....................... 600/28 |
| 5,865,733 A | * | 2/1999 | Malinouskas et al. ....... 600/300 |
| 5,873,736 A | * | 2/1999 | Harrison ..................... 381/151 |
| 5,898,787 A | * | 4/1999 | Stanford ..................... 381/332 |
| 5,999,801 A | * | 12/1999 | Johnson ..................... 455/90 |
| 6,494,719 B1 | * | 12/2002 | Logan ........................ 434/262 |

FOREIGN PATENT DOCUMENTS

JP 11-205878 * 7/1999 ............ H04R/1/00

* cited by examiner

*Primary Examiner*—Xu Mei
(74) *Attorney, Agent, or Firm*—Knobbe Martens Olson & Bear LLP

(57) ABSTRACT

A fetal communication device includes a wireless microphone for transmitting audio signals to be communicated to the baby. The communication device includes a rigid housing adapted for a comfortable fit to the mothers abdomen. The communication device also includes a timer and sound level monitor to help prevent undesired volume levels and durations of stimulation.

6 Claims, 7 Drawing Sheets

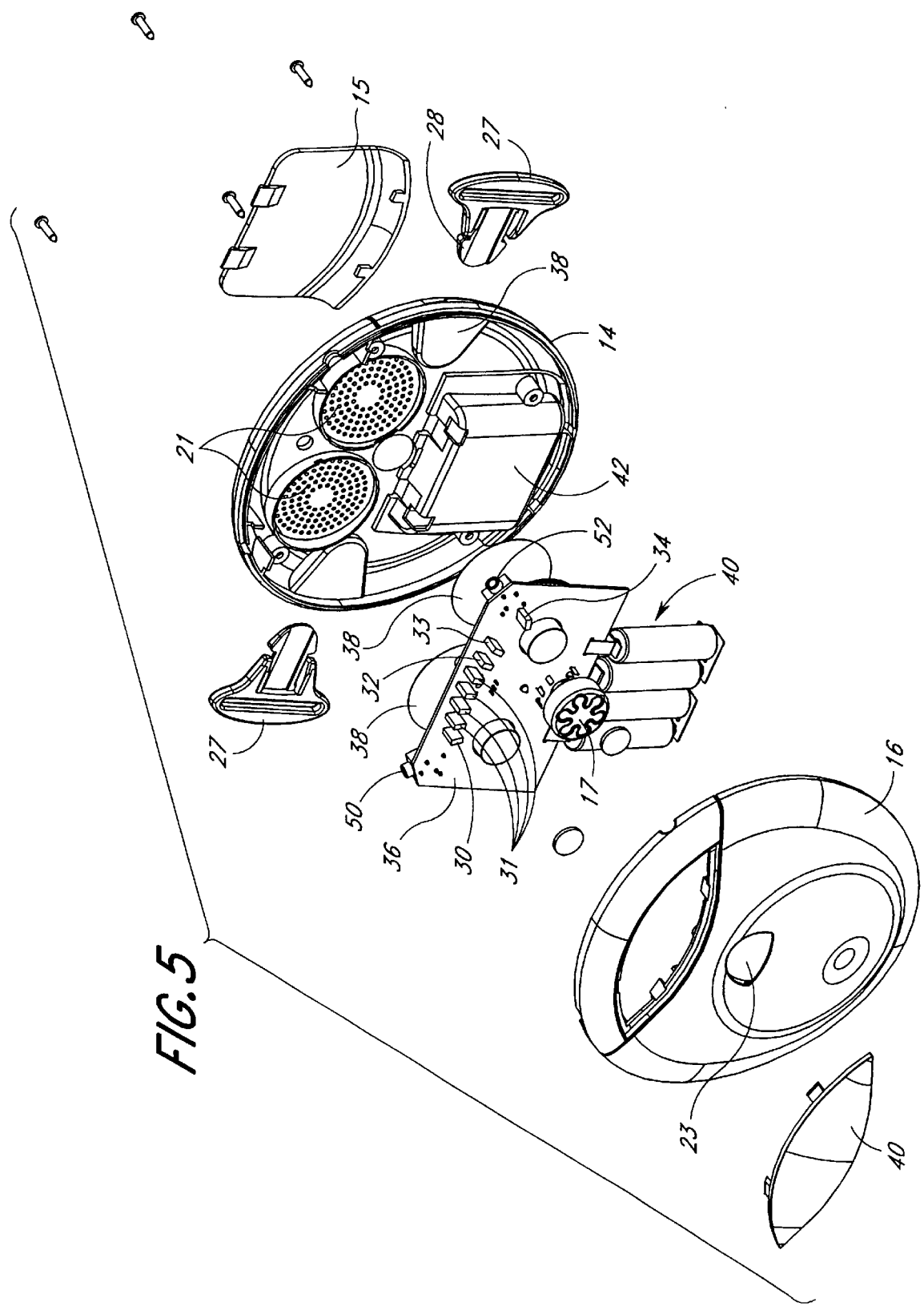

FETAL COMMUNICATION APPARATUS

BACKGROUND OF THE INVENTION

The present invention relates to methods and apparatus for providing auditory stimulation to a fetus in utero. A significant increase in the understanding of brain development of the fetus in utero has occurred in the last ten years. In contrast to past beliefs, children are no longer considered to be born with blank, undeveloped minds. In fact, some research indicates that children begin to learn from a very early stage in life, perhaps as early as the first few months after conception.

Accordingly, a few devices for providing stimulation to the fetal mind during gestation have been developed. For example, U.S. Pat. No. 5,491,756, entitled "System for Delivering Sound to and Monitoring Effects on a Fetus" discloses a belt enclosed device containing speakers for imparting sound to a fetus and a detachable sound generating device. This invention is described as an improvement over the prior art based in part on its use of a belt suspending attachment which served to redistribute the weight of the device. This patent also does describes a method of monitoring the aftereffects of sound stimulation on a fetal child upon which the device was used. In U.S. Pat. No. 4,934,998, issued Jun. 19, 1996 entitled "Prenatal Audio Apparatus," a method is described wherein a mother uses the device to listen to the material being played to the fetus using a pair of head phones which are attached to the audio source on the belt.

The fetal stimulation devices which have been previously known have included several disadvantages. Excess weight and bulkiness has been a common problem. Using the devices of the prior art alternatively for music or other pre-recorded material as well as a parent or other caregiver's voice has been less than convenient. Furthermore, control over the volume and duration of fetal stimulus has been insufficient. Thus, there remains a need for a system for providing fetal auditory stimulation which can be used comfortably and safely.

SUMMARY OF THE INVENTION

The invention includes methods and apparatus for exposing an unborn child to audio stimulation. In one embodiment the apparatus comprises a housing, a wireless microphone external to the housing; and a wireless receiver mounted in the housing and configured to receive signals from said wireless microphone. To stimulate the fetus, the apparatus further comprises at least one speaker coupled to the wireless receiver and mounted to the housing, wherein the housing is adapted for contact with an abdomen wall of a pregnant female.

The present invention also includes methods and apparatus for limiting fetal stimulation to desired time intervals and sound levels. Thus, the invention includes an apparatus for imparting auditory stimulation to a fetus comprising at least one speaker and a timer adapted to monitor time of operation of the speaker, so as to attenuate sound transmission by the speaker after a predetermined period of operation. Additionally, the invention comprises an apparatus for imparting auditory stimulation to a fetus comprising at least one speaker and a sound level monitor adapted to monitor sound levels emitted by the speaker. The timer and sound level monitor may be connected to disable circuitry to attenuate the audio output when the device has been in operation for a preselected time period, or when a undesired volume is output from the speaker.

BRIEF DESCRIPTION OF THE DRAWINGS

FIG. 5 is an exploded view of the fetal stimulator of FIG. 3.

DETAILED DESCRIPTION OF THE PREFERRED EMBODIMENT

Preferred embodiments of the present invention will now be described with reference to the accompanying Figures, wherein like numerals refer to like elements throughout. The terminology used in the description presented herein is intended to be interpreted in its broadest reasonable manner, even though it is being utilized in conjunction with a detailed description of certain specific preferred embodiments of the present invention.

The present invention relates to apparatus and methods for imparting auditory stimulation to a fetus. The present apparatus and methods are particularly well suited for use in exposing a fetus to a variety of musical and vocal stimulus. Such in utero exposure may provide the basis of a lifelong appreciation for the musical arts as well as: forging early bonds between the child and his or her parents while the child is still in the womb. The present invention may also be used to stimulate learning in a fetus. Exposure of a child in utero to instructional audiotory stimulation may result in an enhanced ability to acquire language and other skills.

In use, the communication apparatus of the present invention is positioned in contact with the abdominal wall of an expectant mother. A signal is transmitted to the device from an audio source. The audio source may be hard-wired to the communication apparatus, although in some advantageous embodiments, the transmission is implemented using electromagnetic radiation. That signal is received and monitored by the communication apparatus of the present invention and is subsequently transmitted to a fetus through the abdominal wall of its mother for a predetermined period of time at a predetermined auditory level. As will be explained further below, if the signal exceeds either of those predetermined levels, it is automatically disabled. The wireless fetal communication apparatus disclosed herein thus provides a convenient, comfortable, and safe method to communicate with ones baby in utero.

Figure 1:
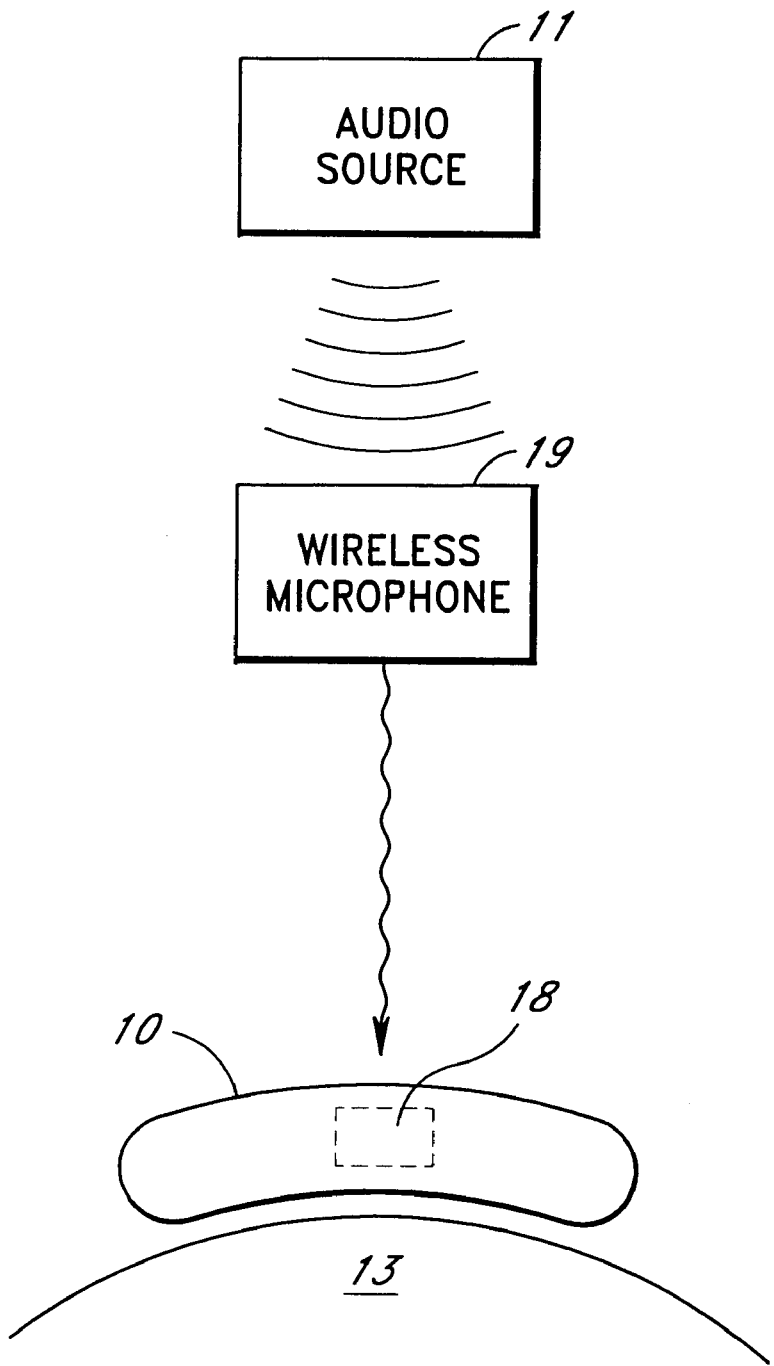
FIG. 1 is a block diagram showing one embodiment of an apparatus for generating and imparting sounds to a fetus according to the invention.

Referring now to FIG. 1, there is illustrated a block diagram of one embodiment of the system of the present invention for transmitting audiotory stimulation to a fetus. In this embodiment, an audio source 11 which is separate from the communication apparatus 10 of the present invention transmits an acoustic signal to a wireless microphone 19.

The wireless microphone 19 then transmits the signal to a wireless receiver 18 contained in the communication apparatus 10, which is placed in contact with the abdominal wall 13 of the mother.

In some advantageous embodiments, the audio source is a parent or other caregiver that is speaking into the wireless microphone 19. The wireless microphone 19 picks up the voice of the speaker and transmits that sound to the fetus. The wireless microphone 38 may be worn on the shoulder, chest, or arm of the mother, father, or significant other who wishes to speak to the baby. The person wearing the wireless microphone speaks into it, and the wireless microphone 19 translates that acoustic signal into an electromagnetic signal which is transmitted to the wireless receiver 18 of the communication apparatus 10. This capability permits the fetus to be exposed to the voice patterns of his or her parents, grandparents, and other members of the family and friends that will play a role in the life of the child after birth. This may stimulate voice pattern recognition in the fetus which, in turn, may enhance voice recognition after birth. This feature is especially useful for those parents who must travel for long periods of time, such as members of the armed forces. On a trip away from home the absent loved one may speak into a phone, have their voice picked up by the microphone of the device held to the telephone receiver at home, thus communicating with the child in utero. Wireless microphones suitable for use with the invention are commercially available. It will be appreciated that the wireless microphone may use any number of transmission methods, including AM, FM, phase modulation, infrared, or any other information transfer method.

A variety of other audio sources are also contemplated for use with the present invention. For example, one could use the present invention with audio sources including radios, high fidelity stereo systems, compact disc systems, or other like audio sources. In these embodiments, the wireless microphone 19 is placed proximate to the speakers of the audio system, and transmits the music or other audio input to the communication device 10.

It can be appreciated that the configuration shown in FIG. 1 provides a number of advantages over other methods of fetal stimulation. One such advantage is that the present invention is is conveniently usable with a large variety of audio sources. Unlike other devices which produce auditory stimulation from a dedicated audio source, the communication apparatus 10 of the present invention may be used with a number of different types of audio sources. This freedom of use permits a mother using the device to choose the source of the audio signal which will be transmitted to her baby in utero, thereby expanding the scope of subject matter which is available for transmission to a fetus. For example, when a mother using an audio source dedicated device (such as a cassette player) desired to transmit a song recorded on a Compact Disc to her baby, she would first have to record it on a tape cassette and then play it for her baby. Since the present invention may be used with a variety of audio sources, the mother in this example would simply place the wireless microphone 19 next to the CD player, and activate the communication apparatus 10. This freedom of audio source choice provides the user and the fetus greater opportunities for experience and growth than other devices in the prior art while reducing the costs of use. This feature also allows the present invention to be convenient to use in a wider variety of settings such as driving, while at work, while traveling, while out of doors, etc.

The above described wireless communication features also allow the apparatus of the present invention to be useful after birth as a baby monitor or as a source of lullaby or other music in the infant's crib. As a baby monitor, the wireless microphone 19 may be attached to the crib near the baby, and the communication apparatus 10 may be placed in a different room with the parent or other caregiver. As a source of soothing sound such as lullaby music, the wireless microphone may be placed in another room next to, for example, a CD player, and the communication apparatus 10 may be attached to the crib near the baby. For these uses, the communication apparatus 10 and wireless microphone 19 may be provided with additional hooks or straps (not shown) to allow convenient attachment to the rails of a crib. A wide variety of crib securement devices may be used, and they may be integral to the communication apparatus 10 and wireless microphone 19 or removeable therefrom.

Figure 2:
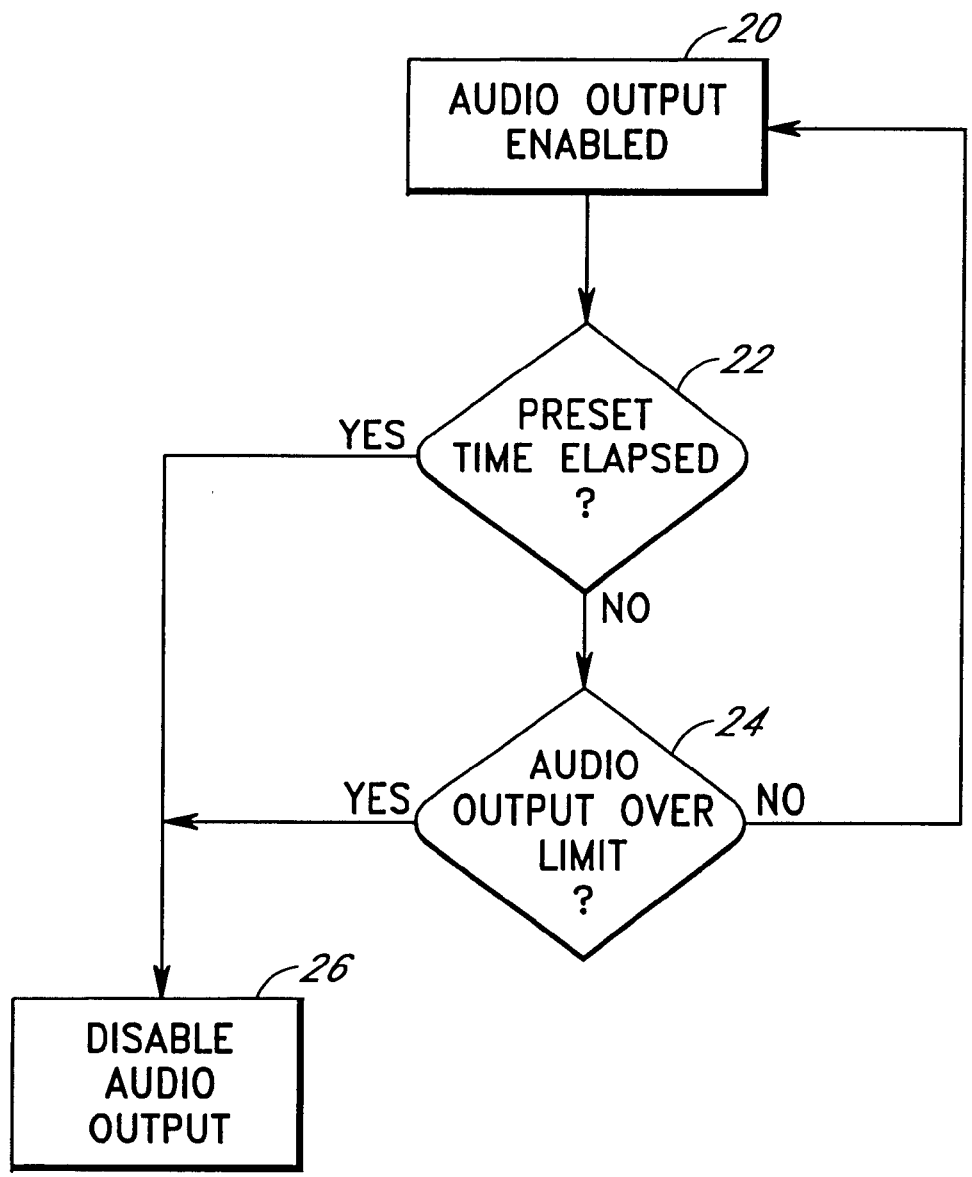
FIG. 2 is a flow chart illustrating a mode of operation of a fetal stimulation apparatus according to the invention.

It is another aspect of the present invention that the volume and duration of audio stimulation to the fetus is automatically limited. This is illustrated in FIG. 2, which is a flowchart of one mode of operation of the invention. When initially placed in the on state, the communication apparatus 10 has an enabled audio output, as shown at step 20 of FIG. 2. The communication device 10 may include detection circuitry which, at step 22, monitors the time of operation since the unit has been powered on, and detects when that time is beyond a preset time limit. If the time limit has elapsed, the communication apparatus 10 disables the audio output at step 26. A time limit of approximately 20 minutes has been found advantageous. The communication apparatus may additionally include detection circuitry which monitors, at step 24, whether the audio output is over a preset limit, thus indicating a volume level which may be undesireable. If the volume level is beyond the preset limit at step 24, the communication apparatus again disables the audio output at step 26. In some embodiments, the detection circuitry is configured to disable the output when the output volume of the communication apparatus exceeds approximately 70–75 dB. If neither the time limit of step 22 nor the sound level limit of step 24 have been exceeded, the communication apparatus continues in the mode illustrated at step 20, wherein the audio output is enabled, and the fetus continues to receive stimulation from the communication apparatus 10.

Figure 4:
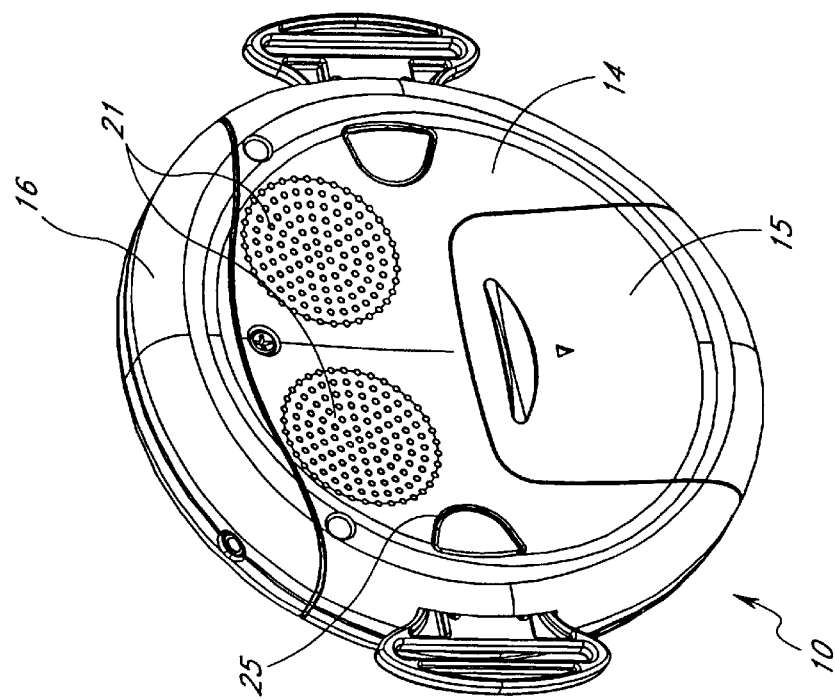
FIG. 4 is a rear view of the fetal stimulator of FIG. 3.
Figure 3:
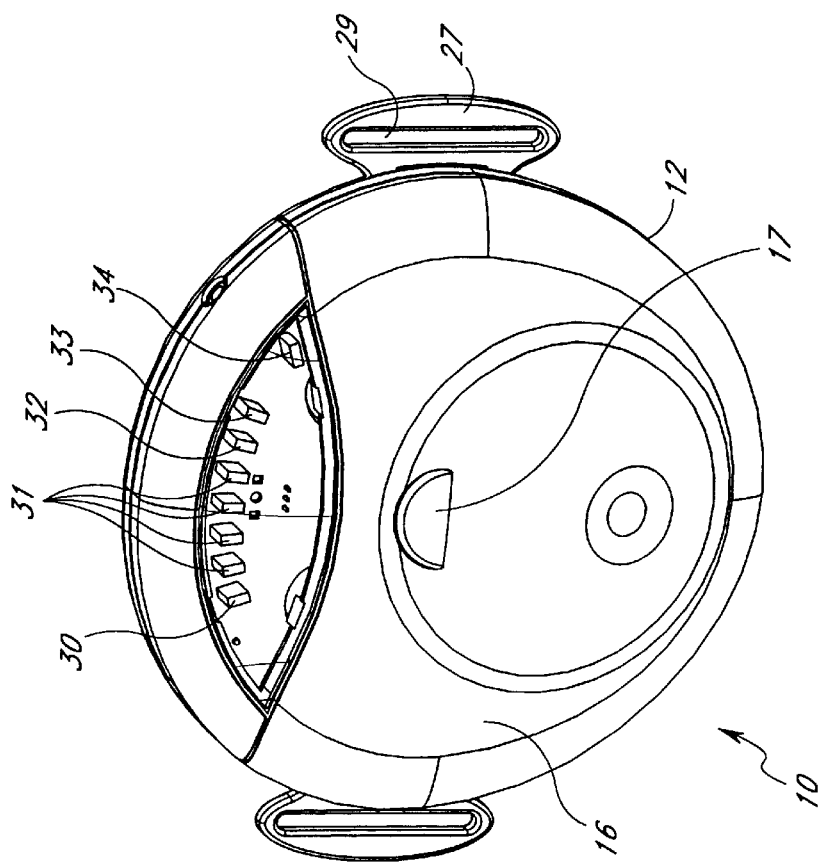
FIG. 3 is a front view of one embodiment of a fetal stimulator according to the present invention.

Referring to FIGS. 3 and 4, perspective views of one specific embodiment of a communication apparatus according to the invention is illustrated. The communication apparatus 10 shown in these figures comprises a substantially rigid housing 12 having an inner surface 14 and an outer surface 16. The rigid housing 12 may be molded or machined from a variety of materials known to one skilled in the art. A suitable material of construction is light-weight, shatter resistant, and non-conducting. Examples of suitable materials include plastics, light-weight metal alloys, and various synthetic and natural polymer materials.

Refering now specifically to FIG. 3, a front view is provided which displays the outer surface 16 of the housing 12. On the outer surface 16 of this embodiment are a number of control mechanisms that allow the user to regulate and visually monitor the functioning of the device. For example, the housing 12 may include an on/off switch and volume control 17 that permits the user to manually activate or deactivate the communication apparatus 10 and control the sound level from the device. The on/off switch and volume control 17 is mounted to a printed circuit board inside the housing 12 and extends partly through an opening in the housing for user access. When the device is turned on, a light emitting diode (LED) 30 is energized to indicate the on state of the device 10.

The embodiment depicted in FIG. 3 also includes a visual indicator of the sound level transmitted to the fetus as a series of six light emitting diodes 31, 32, 33 that are used to visually indicate the sound levels produced by communication apparatus 10. In this embodiment, the LEDs 31, 32, 33 illuminate in response to increasing levels of sound being transmitted to the fetus. Thus, the number of LEDs illuminated increases as the level of sound transmitted to the fetus increases. The first four LEDs 31 of this series of six are advantageously green in color. The fifth LED 32 may be yellow, indicating that the volume is reaching levels close to the maximum desireable levels. When the auditory signal increases further, a red LED 33 illuminates. As will be explained in more detail below, increases beyond a preset level above that required to energize the red LED 33 will cause the audio output to be disabled until a lower output level is detected.

Although the visual indicator of this embodiment is shown as a series of LEDs, other means of visually indicating transmission levels are contemplated. These alternatives include gauges or dials that would also permit a mother using the device to monitor the sound levels transmitted to her child. Thus, volume adjustment becomes much more convenient for the mother as compared to prior art devices because a direct indication of the sound levels being transmitted to the baby is available.

An additional LED 34 may also be provided. This LED 34 may be used to indicate when the preset operational time limit discussed above has elapsed and audio output has been disabled in response to this elapsed time. In some embodiments, this LED 34 is yellow in color.

FIG. 4 shows the inner surface 14 of the communication apparatus 10. In the embodiment shown, the inner surface 14 is curved into a substantially concave configuration so as to accommodate the abdomen of the mother. The curved shape of inner surface 14 allows the device to fit snugly against the abdominal wall of a mother using the device. The curved shape may also help to distribute the weight of the apparatus around the woman's belly to ease the load of carrying the apparatus. These design features make using the communication apparatus of the present invention a comfortable and pleasant experience.

The inner surface 14 and its shape also serve to contain the sound of the auditory stimulation. When the communication apparatus 10 is in use, the curved inner surface 14 helps contain the sounds being transmitted to the child and reduces their transmission into the external environment. The shape of the apparatus resulting in the retention of a substantial amount of the auditory signal transmitted to the fetus is an advantageous feature of the present invention. When used in the work place, the shape of the apparatus and the resulting seal formed during use prevent co-workers from hearing and thus being disturbed by the auditory stimulation transmitted to a mother's fetus. Similarly, the shape and seal forming character of the present invention may prevent a mother's other children or visitors from being disturbed by the auditory stimulation being transmitted to a child in utero.

The embodiment of the present invention depicted in FIG. 4 includes a battery compartment panel 15 present on the inner surface 14. Additionally, two speaker outputs 21 are provided on the inner surface 14 of the housing 12. The speaker outputs 21 are positioned on the inner surface 14 so as to be in auditory contact with the abdominal wall of a pregnant woman when the communication apparatus 10 is positioned for use. The scope of the invention is not limited by the number of speakers shown in this figure and contemplates the use of a single speaker as well a plurality of speakers to create fetal auditory stimulation. A single speaker embodiment may be advantageous in that the total size of the device may be reduced. It can be appreciated that reductions in the size of the device by using a single speaker and/or additional miniaturization of circuit components may render the device more comfortable to wear.

The inner surface 14 of the device 12 may be textured with small ridges or bumps which contact the mother's abdominal wall. Such ridges or bumps will gently vibrate with the sound being transmitted from the speakers 21. This feature provides additional tactile stimulation to the abdominal wall, providing a relaxing sensation to the mother.

In some embodiments, the inner surface 14 of the communication apparatus 10 may also comprise a stethoscope style abdominal contact surface (not shown). Sounds from the fetus received by the stethoscope style contact surface may be transferred to the exterior of the device via stethescope tubing, or sounds from the contact surface may be routed to an internal microphone which has an electrical output routed to the exterior of the device. In the first case, a conventional stethoscope attachment may be provided which connects to the end of the internal stethoscope tubing at the exterior of the device. If an internal microphone is provided, headphones may be provided which attach to the microphone output at the exterior of the device. As another alternative, the microphone output could be amplified and routed to a speaker mounted, for example, on the front panel of the device, so that received sounds are made audible to both the mother and others nearby. Embodiments including this feature may thus be used to listen to the baby's heartbeat and movement while in the womb.

The fetal communication device may also be provided with belt attachment members 27 used to attach a belt (not shown) to the communication apparatus 10. As depicted in FIGS. 3 and 4, the belt attachment members 27 comprise protuberances extending outward from the housing. Each belt attachment member may be a molded part of the housing 12 or may be a separate piece that is reversibly inserted into the housing 12, as will be described in more detail below in conjunction with FIG. 5. The belt attachment members 27 advantageously comprise a belt aperture 29 into which the belt is inserted and attached with a buckle, velcro, or other suitable means. When a belt is attached to the apparatus, it serves to hold the inner surface 14 of the housing 12 in contact with the abdomen wall of the mother. When a reversibly detachable belt attachment site 27 is used in the present invention, belt removal apertures 25 may also be present on the inner surface 14 of the communication apparatus 10. These apertures 25 may be used to facilitate the removal of the belt attachment members 27 from the apparatus, thereby providing an easy method for the user to remove the device from her body while retaining the belt in a properly adjusted length.

FIG. 5 is an exploded view of the device depicted in FIGS. 3 and 4, and illustrates the reversibly attached belt attachment members 27. Depicted in FIG. 5 is one embodiment of such reversibly detachable belt attachment members 27. In this embodiment, a resilient flared tongue 28 on the belt attachment member 27 may be introduced into a receiving bay 39 in the housing 12. The flared tongue 28 is inserted into the bay 39 until the flared portion of the structure enters and snaps into the belt removal aperture 25 shown in FIG. 4. The shape of the tongue 28 and the engagement of the tounge 28 with the belt removal aperture 25 hold the belt attachment site 24 in place in the housing 12.

Removal of the belt attachment member 27 proceeds along similar lines as just described, although in reverse order. To remove a belt attachment member 27 from the housing 12, the flared tongue 28 is first depressed by inserting one's finger into the belt removal aperture 25. Next, force is applied to push the tounge out of the aperture 25, and the belt attachment member 27 is slid out of the receiving bay 39, freeing the belt attachment member 27 from the housing 12.

The belt attachment members 27 may be constructed of materials similar to those used to construct the housing 12. The belt (not shown) may be constructed of a material that is similarly light-weight and non-conductive. The belt material should also be pliable to permit comfortable use of the belt when attached to the communication apparatus 10. Suitable materials for belt construction include natural and synthetic fabrics and polymers such as cotton or nylon. Other suitable fabrics known in the art are also contemplated.

Referring again to FIG. 5, it can be seen that the inner surface 14 and outer surface 16 of the communication apparatus enclose a printed circuit board 36 which provides a mounting surface for the electrical components of the communication apparatus. Provided as part of the front surface is a transparent or translucent cover 41 which allows the user to see the LEDs 30, 31, 32, 33, 34 described above. The outer surface 16 also comprises an aperture 23 through which the on/off switch and volume control 17 is accessible. In the embodiment depicted, the volume control device 17 is rotated clockwise or counter-clockwise in the volume control aperture 23 to increase or decrease the sound levels transmitted. The present invention contemplates additional methods of controlling the sound levels transmitted to a fetus. Those methods include sliding volume control mechanism and push button mechanisms which result in an incremental change in the levels of sound transmitted to the fetus.

Also mounted to the printed circuit board 36 are two speakers 38 which rest in the speaker outputs 21. In general the speaker outputs are shaped to conform to the outer perimeters of the speakers 38. Typically the speaker outputs 21 will contain a number of holes, slits, or other apertures which permit auditory stimulation to be transmitted from the speakers 38 to the baby.

The batteries 40, which may comprise four AA size batteries, are shown coupled to the printed circuit board 36 as well, although it will be appreciated that in normal use they are placed in the battery holder 42 on the inner surface 14 of the housing 12 and make an electrical connection to terminals on the printed circuit board 36.

Figure 6:
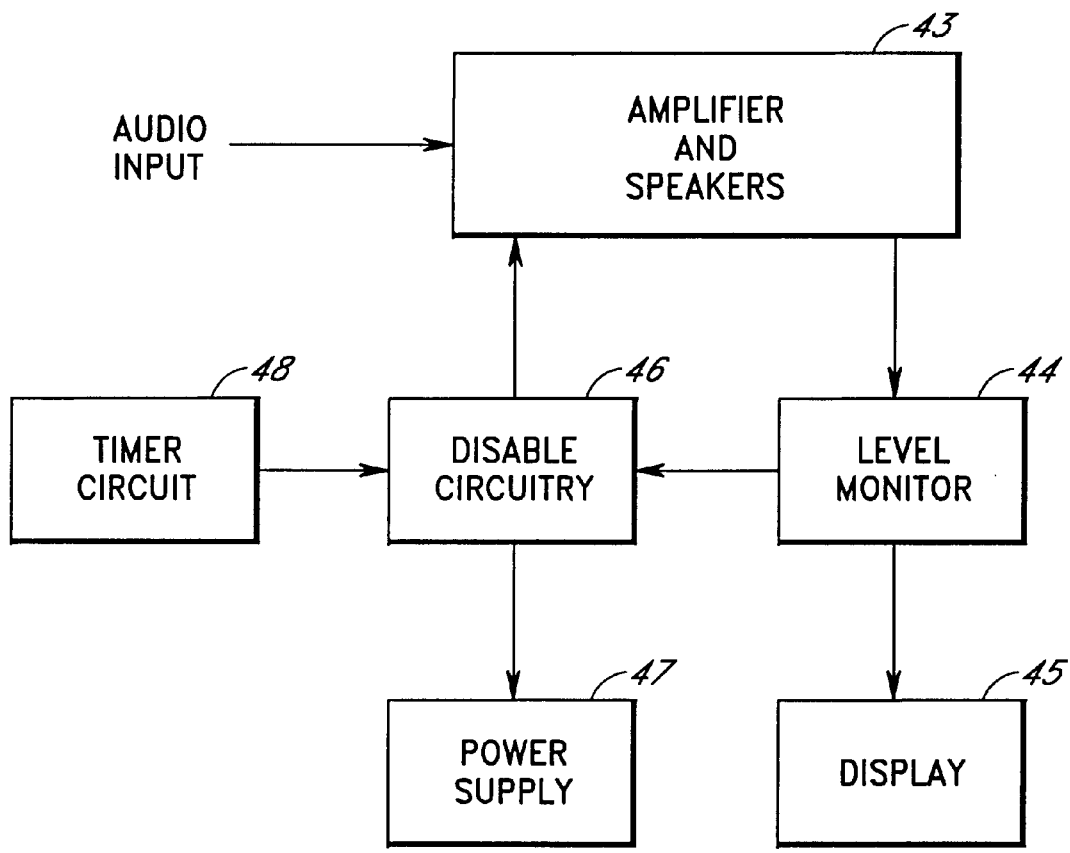
FIG. 6 is a block diagram of the circuit in one embodiment of a fetal communication apparatus according to the invention.

FIG. 6 illustrates a block diagram of the circuitry of the communication device 10 according to one embodiment of the invention. As shown in this Figure, an audio signal is input to amplifier and speaker circuitry 43. The amplifier/speaker circuitry 43 is coupled to a level monitoring circuit 44 which monitors the volume output by the device. This may be performed by sensing the speaker or amplifier input. The level monitor circuit 44 is coupled to a display 45 which allows the user to ascertain the volume being output by the device 10. In the embodiment of FIGS. 3–5, this display comprises the series of LEDs 31, 32, and 33.

The level monitor circuit 44 is also coupled to a disable circuit 46, which attenuates, terminates, or otherwise disables the speaker output when the volume exceeds a predetermined limit. This may be accomplished by either inhibiting amplification, or inhibiting the power supply of the communication device 10. Accordingly, disable circuitry 46 may be coupled to either or both the amplifier/speaker circuit 43 and the power supply circuit 47. The communication device 10 may also be provided with a timer circuit 48 which is also coupled to the disable circuitry 46. The timer circuit 48 monitors the amount of time the unit has been activated, and signals the disable circuitry 46 to again disable the output of the device when a predetermined time has elapsed in a manner analagous to that described with reference to the excessive volume output.

Figure 7:
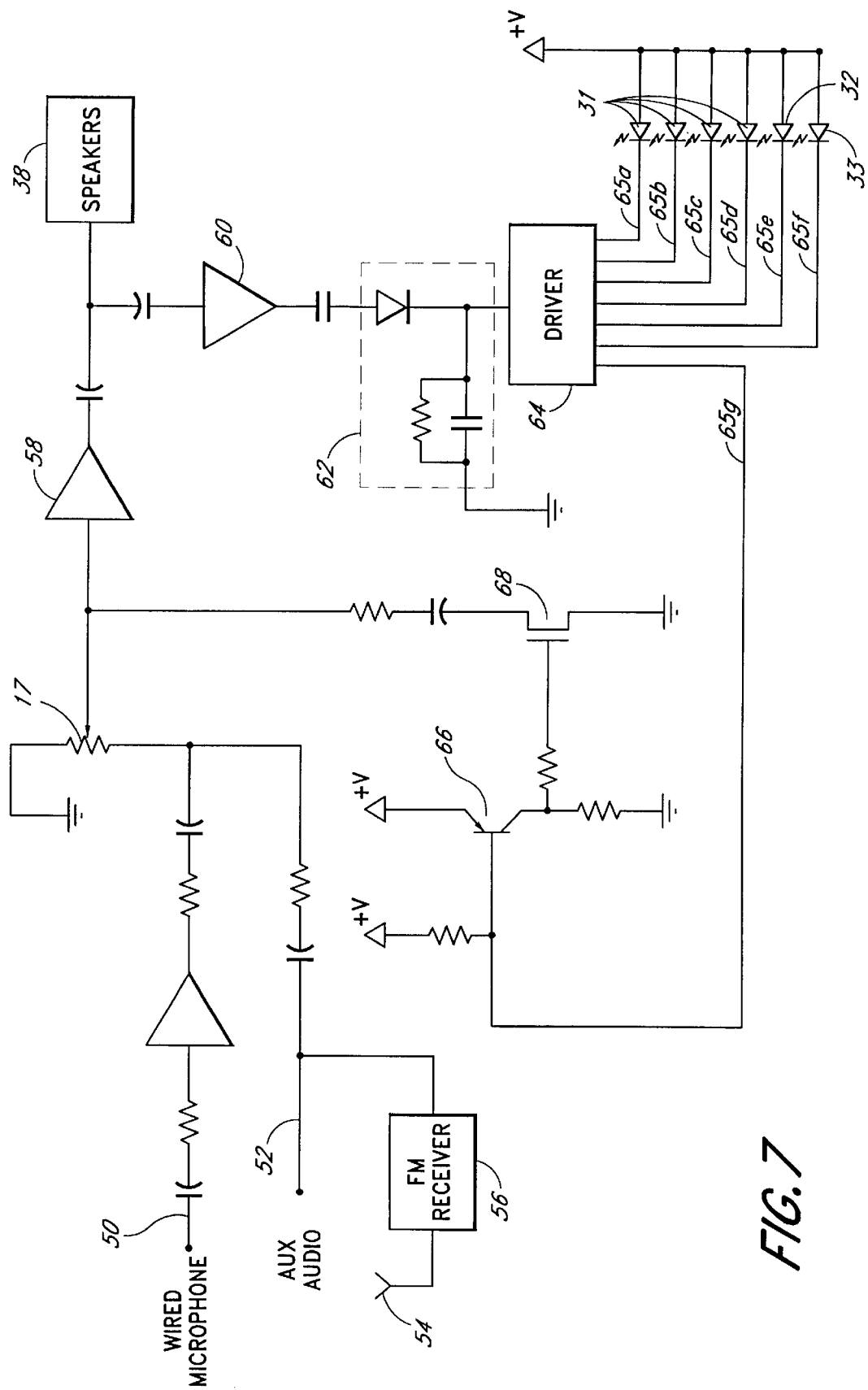
FIG. 7 is a simplified schematic of one embodiment of the audio amplifier circuit of a fetal stimulator according to the invention.
Figure 8:
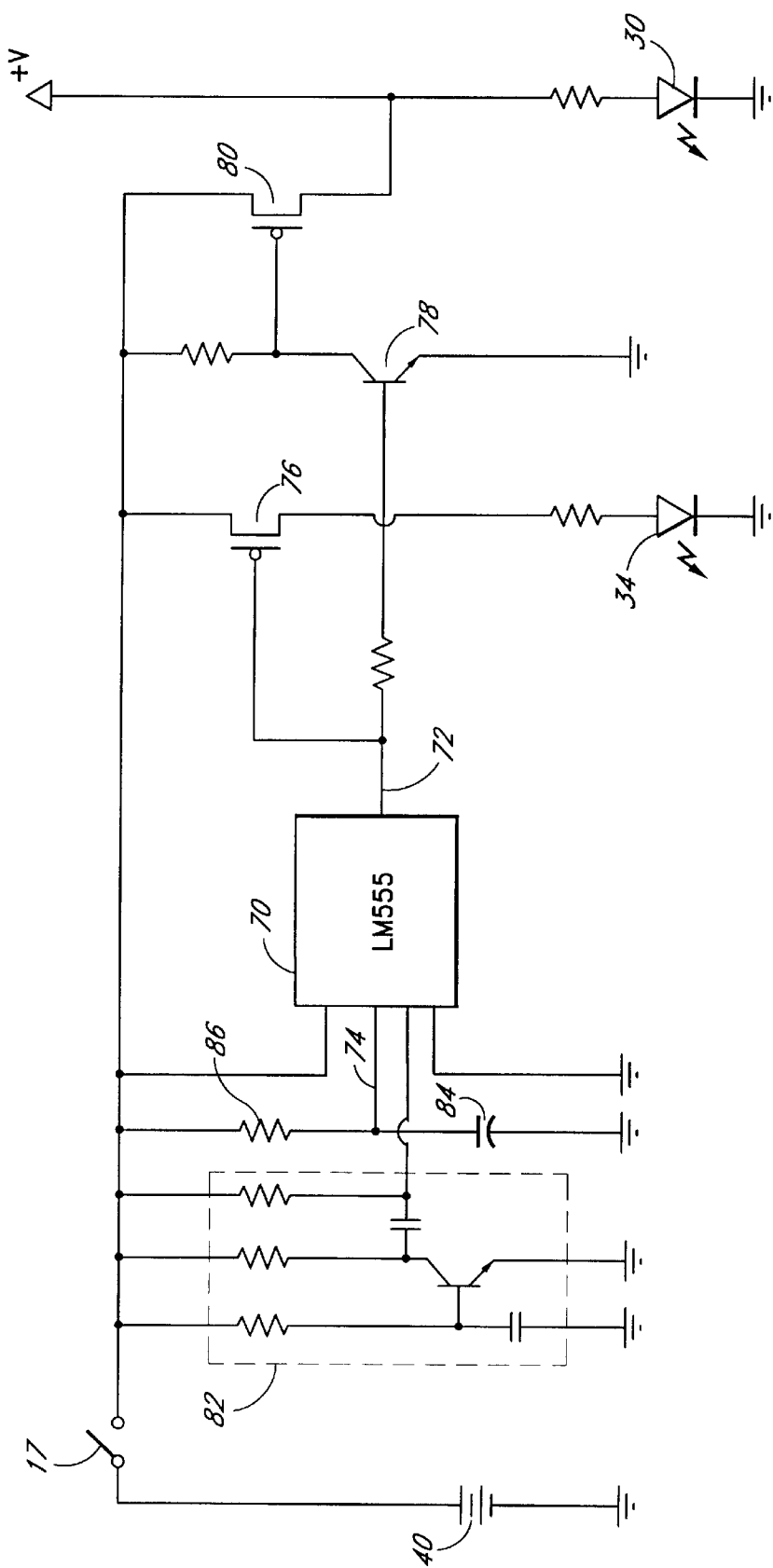
FIG. 8 is a simplified schematic of one embodiment of a power control circuit of a fetal stimulator according to the present invention.

FIGS. 7 and 8 are simplified schematics of specific circuits suitable for use in the communication device 10 to implement the features illustrated in FIGS. 2 and 6. It will be apparent to those of skill in the art that many different alternatives exist for implementing the novel features of the invention using conventional circuit components, and that the specific implementation shown is only exemplary.

Referring now to FIG. 7, the communication device 10 receives input signals from either a wired microphone at jack 50, an auxiliary audio input at jack 52, or from the wireless microphone via an antenna 54. The antenna 54 is coupled to a conventional FM receiver 56, such as the part number TDA7088T manufactured by Phillips. The audio output of the FM receiver 56 is routed to an amplifier 58 via the volume control potentiometer 17 discussed above. Suitable audio amplifier circuits are well known, with one suitable embodiment being the LM386M-1 from National Semiconductor. The output of the audio amplifier 58 drives the speakers 38.

Also shown in FIG. 7 is the circuitry which drives the volume display LEDs 31, 32, 33 described above. This function may be performed by routing the audio output to another amplifier 60 with an output coupled to a peak detection circuit 62. The output of the peak detector 62 is routed to a commercially available LM3916M display driver integrated circuit 64. The driver integrated circuit 64 has seven outputs 65a–65g, which are sequentially pulled low in response to a rising voltage level ouptut by the peak detection circuit 62. Output 65a is pulled low first, with 65g being pulled low last as the output of the peak detection circuit rises. Thus, the green LEDs 31 described above are connected to outputs 65a–65d respectively, the yellow LED 32 is connected to output 65e, and the red LED 33 is connected to output 65f.

The prevention of excessive volume output from the communication apparatus may be implemented by using the final output 65g of the driver 64 to trigger the disabling of the audio output to the speakers. When output 65g is pulled low in response to a high voltage output of the peak detection circuit 62, transistor 66 is turned on, which turns on an n-channel field effect transistor (FET) 68 to provide a low impedance path between ground and the input to the audio amplifier 58. It will be appreciated that other methods of disabling the audio output in response to undesireable volume may be used. The methods may be based on the duration of the high volume output as well as its magnitude. Manual reset may be required if desired.

FIG. 8 is a simplified schematic of the power supply circuit of the communication apparatus 10. This circuit implements the timed audio disablement of the device described above in reference to FIG. 2. The power supply circuit includes the batteries 40 and power switch 17, which as discussed above is integral to the volume potentiometer 17 shown in FIG. 6. Also included is an LM555 timer integrated circuit 70 well known in the art, and available from, for example, National Semiconductor. The timer integrated circuit has an output 72 which is pulled high until a threshold potential is detected at a sensing input node 74, at which point the output node is forced low. As long as the output node 72 remains high, p-channel FET 76 is in the off state, and transistor 78 is in the on-state. The on state of transistor 78 pulls the gate of p-channel FET 80 low, thereby turning FET 80 on, thereby coupling the battery voltage to the remainder of the circuitry in the communication apparatus and energizing the LED 30 described above.

When the switch 17 is closed, pulse generation circuitry 82 starts the timer 70 running as a one shot. At this time, output node 72 is held high by the timer 70, and the capacitor 84 begins charging through the resistor 86. As the capacitor 84 charges, the threshold detection node 74 increases in potential until it passes the threshold and the output node 72 goes low in response. When the output node 72 goes low, transistor 78 and FET 80 are turned off, and FET 76 is turned on. This decouples the battery 40 from the remainder of the communication device circuitry and also energizes LED 34. It can be appreciated that the duration between engaging the switch 17 and the battery decoupling performed by the timer 70 depends on the values of the capacitor 84 and the resistor 86. A suitable time of operation of approximately 10–20 minutes has been obtained using a capacitance of approximately 68 microfarads and a resistance of approximately 20 megohms for the capacitor 84 and the resistor 86 respectively. Once the timer 70 has sensed the threshold voltage at node 74, it may be reset by opening and closing the on/off switch 17. It can thus be appreciated that the circuits of FIGS. 7 and 8 implement the time and volume determinations and audio disabling described above in conjunction with FIG. 2.

The foregoing description details certain preferred embodiments of the present invention and describes the best mode contemplated. It will be appreciated, however, that no matter how detailed the foregoing appears in text, the invention can be practiced in many ways. As is also stated above, it should be noted that the use of particular terminology when describing certain features or aspects of the present invention should not be taken to imply that the broadest reasonable meaning of such terminology is not intended, or that the terminology is being re-defined herein to be restricted to including any specific characteristics of the features or aspects of the invention with which that terminology is associated. The scope of the present invention should therefore be construed in accordance with the appended Claims and any equivalents thereof.

What is claimed is:

1. An apparatus for imparting auditory stimulation to a fetus comprising:

a substantially rigid housing comprising an inwardly curved first surface and a second surface;

at least one display element and at least one control element mounted to said second surface;

a belt attached to said housing for snugly and comfortably holding said inwardly curved surface of said housing adjacent to an abdomen wall of an expectant mother in a generally frontal and easily accessed position on said abdomen wall and for holding said second surface in a position to allow convenient, easily viewable, and easily reachable access to said display and control elements by said expectant mother; and at least one speaker, said at least one speaker being mounted in said housing and against said curved surface.

2. The apparatus of claim 1, further comprising an audio level monitor.

3. The apparatus of claim 2, wherein said audio level monitor comprises an indicator that indicates a sound level transmitted from said at least one speaker.

4. The apparatus of claim 3, wherein said indicator comprises a series of light emitting diodes that illuminate in response to changes in said sound level transmitted from said at least one speaker.

5. The apparatus of claim 2, wherein said apparatus further comprises a disable circuit, wherein said disable circuit attenuates sound level transmitted from said at least one speaker when said audio level reaches a predetermined level.

6. The apparatus of claim 5, further comprising a timer coupled to said disable circuit, said timer acting to attenuate said sound level transmitted from said at least one speaker when said apparatus has been activated for a predetermined period of time.

* * * * *